(12) United States Patent
Yonezawa

(10) Patent No.: US 11,654,265 B2
(45) Date of Patent: *May 23, 2023

(54) CONNECTION STRUCTURE AND GUIDE WIRE HAVING THE CONNECTION STRUCTURE

(71) Applicant: ASAHI INTECC CO., LTD., Seto (JP)

(72) Inventor: Satoshi Yonezawa, Iwate-gun (JP)

(73) Assignee: ASAHI INTECC CO., LTD., Nagoya (JP)

(*) Notice: Subject to any disclaimer, the term of this patent is extended or adjusted under 35 U.S.C. 154(b) by 588 days.

This patent is subject to a terminal disclaimer.

(21) Appl. No.: 16/789,832

(22) Filed: Feb. 13, 2020

(65) Prior Publication Data

US 2020/0179658 A1 Jun. 11, 2020

Related U.S. Application Data

(63) Continuation of application No. 15/425,149, filed on Feb. 6, 2017, now Pat. No. 10,576,253, which is a (Continued)

(51) Int. Cl.
*A61M 25/09* (2006.01)

(52) U.S. Cl.
CPC ... *A61M 25/09* (2013.01); *A61M 2025/09083* (2013.01); *A61M 2025/09108* (2013.01);
(Continued)

(58) Field of Classification Search
CPC ........ A61M 25/09; A61M 2025/09083; A61M 2025/09191
See application file for complete search history.

(56) References Cited

U.S. PATENT DOCUMENTS 2,756,783 A 7/1956 Osuch
5,980,471 A * 11/1999 Jafari .................... A61M 25/09
600/585
(Continued)

FOREIGN PATENT DOCUMENTS

JP 06-023543 A 3/1994
JP 2000-145660 A 5/2000
(Continued)

OTHER PUBLICATIONS

Aug. 8, 2017 Office Action issued in Japanese Patent Application No. 2016-566844.

*Primary Examiner* — Sean P Dougherty
(74) *Attorney, Agent, or Firm* — Oliff PLC

(57) ABSTRACT

A connection structure includes a multi-thread coil formed by winding first metal element wires formed of a first metal and second metal element wires formed of a second metal arranged between a first metal body including the first metal and a second metal body including the second metal. The first metal body is connected to the first metal element wires of the multi-thread coil, and the second metal body is connected to the second metal element wires of the multi-thread coil. The connection structure imparts improved flexibility to the connection between the first and second metal bodies, and an appropriate connection can be provided even when the first and second metal bodies are made of dissimilar metals.

14 Claims, 8 Drawing Sheets

Related U.S. Application Data continuation of application No. PCT/JP2016/077176, filed on Sep. 14, 2016.

(52) U.S. Cl.
CPC ............ *A61M 2025/09133* (2013.01); *A61M 2025/09141* (2013.01); *A61M 2025/09175* (2013.01); *A61M 2025/09191* (2013.01)

(56) References Cited

U.S. PATENT DOCUMENTS

| | | | |
|---|---|---|---|
| 7,607,561 B2 * | 10/2009 | Murayama | A61M 25/09 228/180.5 |
| 8,485,992 B2 * | 7/2013 | Griffin | A61M 25/00 600/585 |
| 9,630,275 B2 * | 4/2017 | Chen | B23K 35/001 |
| 11,202,888 B2 * | 12/2021 | Paul, Jr. | G01R 33/3685 |
| 2003/0069521 A1 * | 4/2003 | Reynolds | A61M 25/09 600/585 |
| 2004/0106878 A1 * | 6/2004 | Skujins | A61M 25/09 600/585 |
| 2004/0193073 A1 | 9/2004 | DeMello et al. | |
| 2008/0051676 A1 | 2/2008 | Melsheimer | |
| 2009/0177119 A1 * | 7/2009 | Heidner | A61M 25/09 600/585 |
| 2011/0301501 A1 * | 12/2011 | Tsunezumi | A61M 25/09 600/585 |
| 2012/0283700 A1 * | 11/2012 | Pawluk | A61M 25/09 604/528 |
| 2012/0310217 A1 * | 12/2012 | Maki | A61M 25/09 604/528 |
| 2014/0046302 A1 | 2/2014 | Green et al. | |
| 2015/0306354 A1 * | 10/2015 | Kanetake | A61M 25/09 604/529 |
| 2018/0071495 A1 * | 3/2018 | Yonezawa | B21F 15/04 |

FOREIGN PATENT DOCUMENTS

| | | |
|---|---|---|
| JP | 2004-298635 A | 10/2004 |
| JP | 2010-84932 A | 4/2010 |
| JP | 2012-254233 A | 12/2012 |

* cited by examiner

CONNECTION STRUCTURE AND GUIDE WIRE HAVING THE CONNECTION STRUCTURE

CROSS REFERENCE TO RELATED APPLICATIONS

This is a Continuation of application Ser. No. 15/425,149 filed on Feb. 6, 2017, which in turn is a Continuation of PCT/JP2016/077176 filed on Sep. 14, 2016. The disclosure of the prior applications is hereby incorporated by reference herein in its entirety.

BACKGROUND

The disclosed embodiments relate to a medical device. Specifically, the disclosed embodiments relate to a connection structure for connecting two metal bodies, and a guide wire having the connection structure.

To date, various connection structures for connecting two metal bodies have been proposed, in particular for forming a flexible connected portion.

For example, Japanese Patent Application Laid-Open No. 2000-145660 describes a flexible shaft (a connection structure) in which an axial part is connected to a coupling through a bendable part comprising a coiled spring, the coiled spring being a multi-thread coiled spring (see, e.g., FIG. 1). The coiled spring serves as a connected portion. This enables the connected portion to be flexible.

However, the flexible shaft described in Japanese Patent Application Laid-Open No. 2000-145660 has the following disadvantage: the axial part is connected to the coupling through the entire circumference of the coiled spring, and thus the flexible shaft may be somewhat difficult to bend due to the repulsive force of the coiled spring. Further, if the axial part and the coupling comprise dissimilar metals, this dissimilarity needs to be taken into account when a connected portion is formed.

Moreover, such a connection structure may potentially be used in a medical device, in particular a guide wire which is used inside a complicatedly winding blood vessel.

SUMMARY

The disclosed embodiments were derived to address the above problems. An object of the disclosed embodiments is to provide a connection structure for connecting two metal bodies in which the flexibility of a connected portion can be further improved, and in particular an appropriate connection can be provided even when the metal bodies are made of dissimilar metals.

In order to achieve the above object, a connection structure between a first metal body formed of a first metal and a second metal body formed of a second metal includes a multi-thread coil formed by winding first element wires comprising the first metal and second element wires comprising the second metal. The multi-thread coil is arranged between the first metal body and the second metal body, and the first metal body is connected to the first element wires of the multi-thread coil, and the second metal body is connected to the second element wires of the multi-thread coil. This can improve the flexibility of a connected portion formed by the multi-thread coil.

The first element wires and the second element wires may be adjacently wound one by one, so that the first element wires and the second element wires are alternately disposed. The first element wires are connected to the first body so as to sandwich the second element wires, and the second element wires are connected to the second metal body so as to sandwich the first element wires. This can prevent distortion of the shape of the multi-thread coil as much as possible, and can improve the flexibility of the connected portion.

The first metal may be a stainless steel alloy, and the second metal may be a nickel-titanium alloy. The connection structure can improve the flexibility of the connected portion, and can also provide an appropriate connection even though dissimilar metals are used that would otherwise be difficult to directly connect.

The connection structure may be used in a guide wire, for example. The guide wire may comprise a core shaft, and a coil body covering a front end of the core shaft. The connection structure connects portions of the core shaft together at a connected portion, thereby improving the flexibility of the connected portion of the core shaft and allowing the guide wire to easily follow a winding blood vessel.

DETAILED DESCRIPTION OF EMBODIMENTS

Below, embodiments of the present invention will be described with reference to the drawings.

Figure 1:
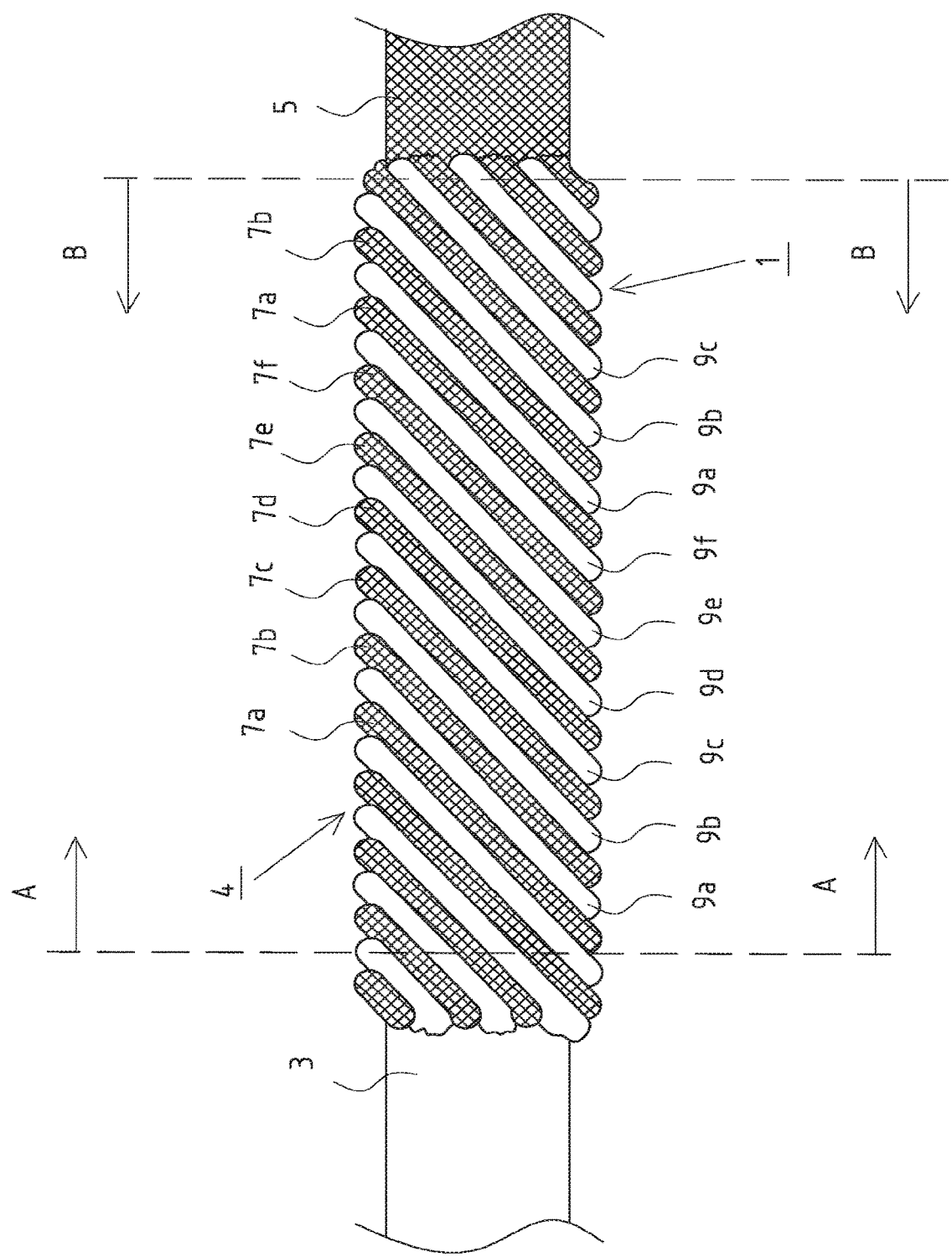
FIG. 1 shows a side view of a connection structure according to the disclosed embodiments.
Figure 2:
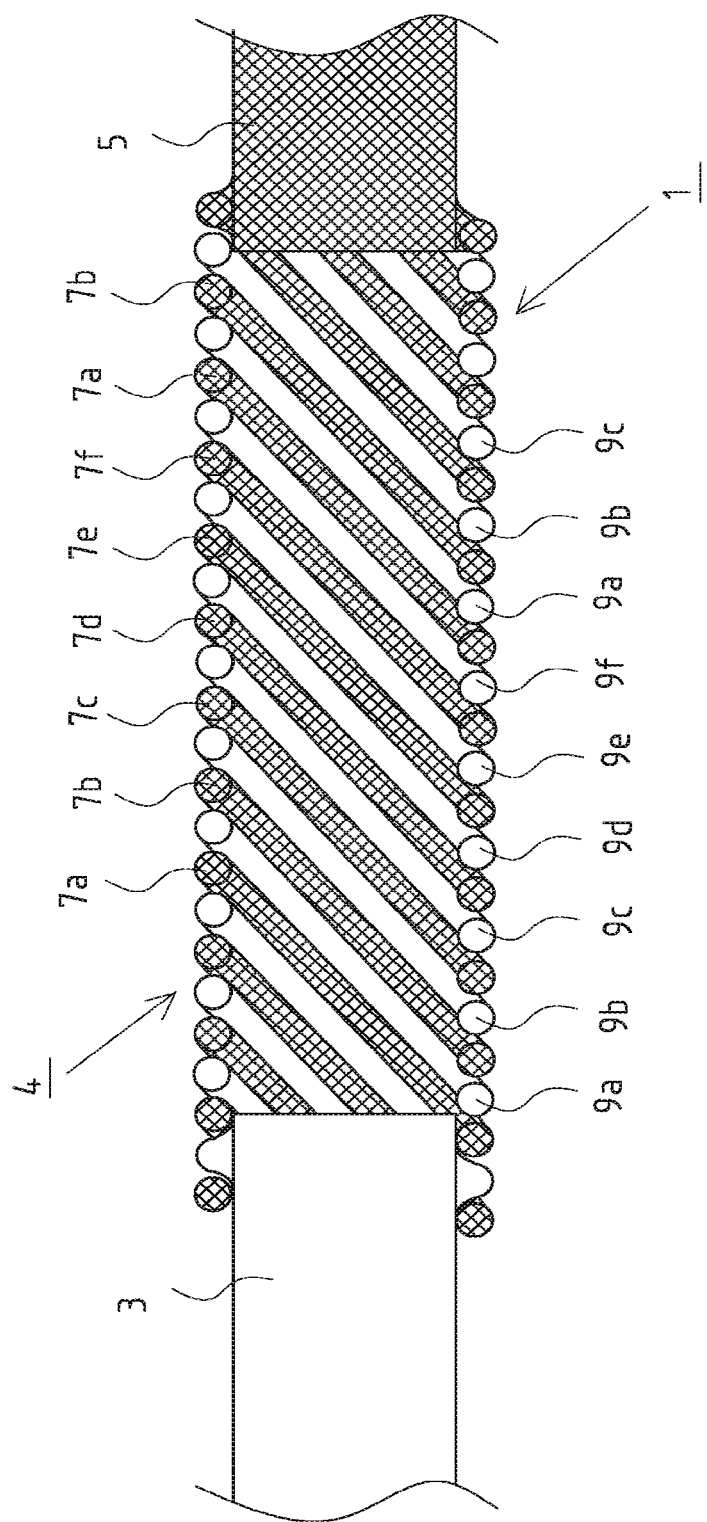
FIG. 2 shows a cross-sectional side view of the connection structure shown in FIG. 1.
Figure 3:
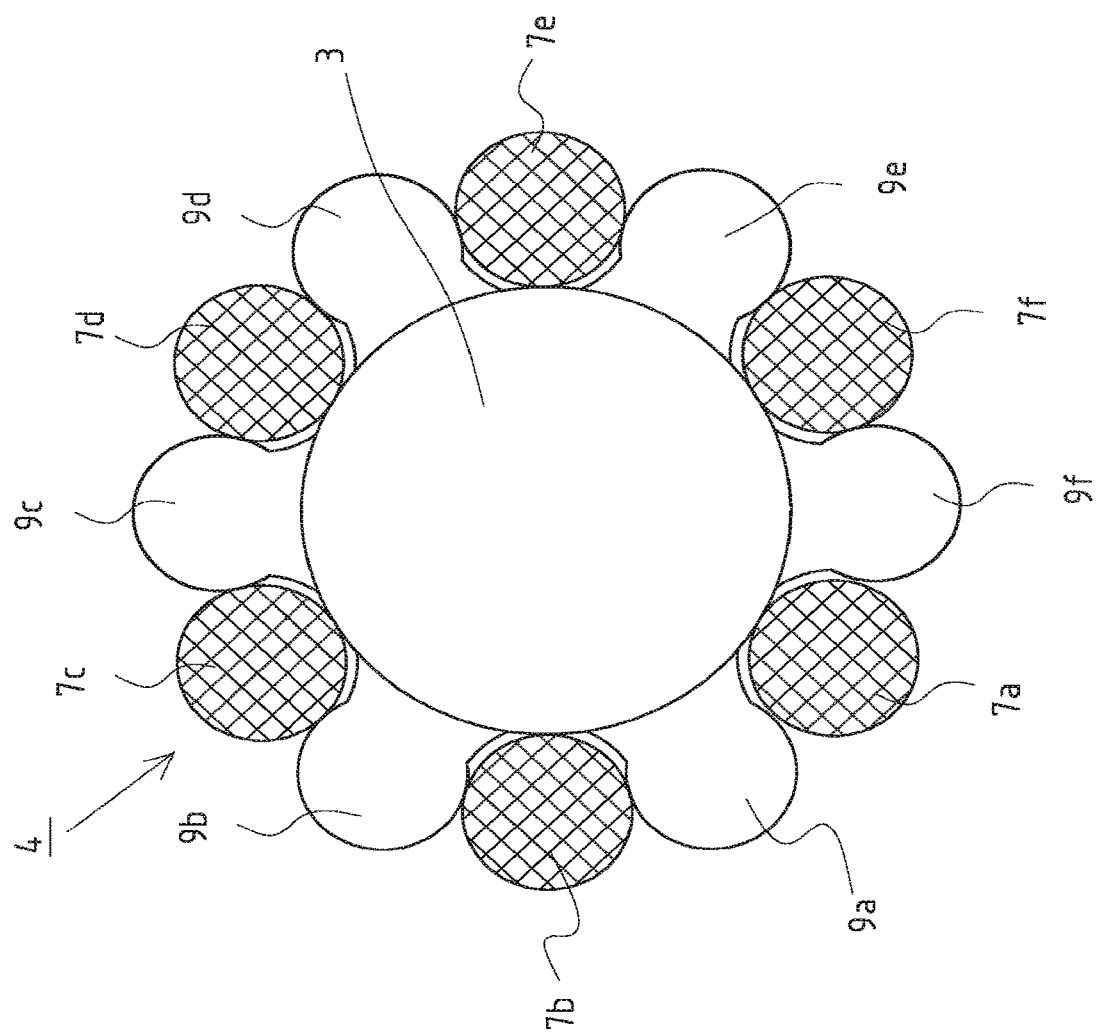
FIG. 3 shows a cross-sectional view along line A-A in FIG. 1.
Figure 4:
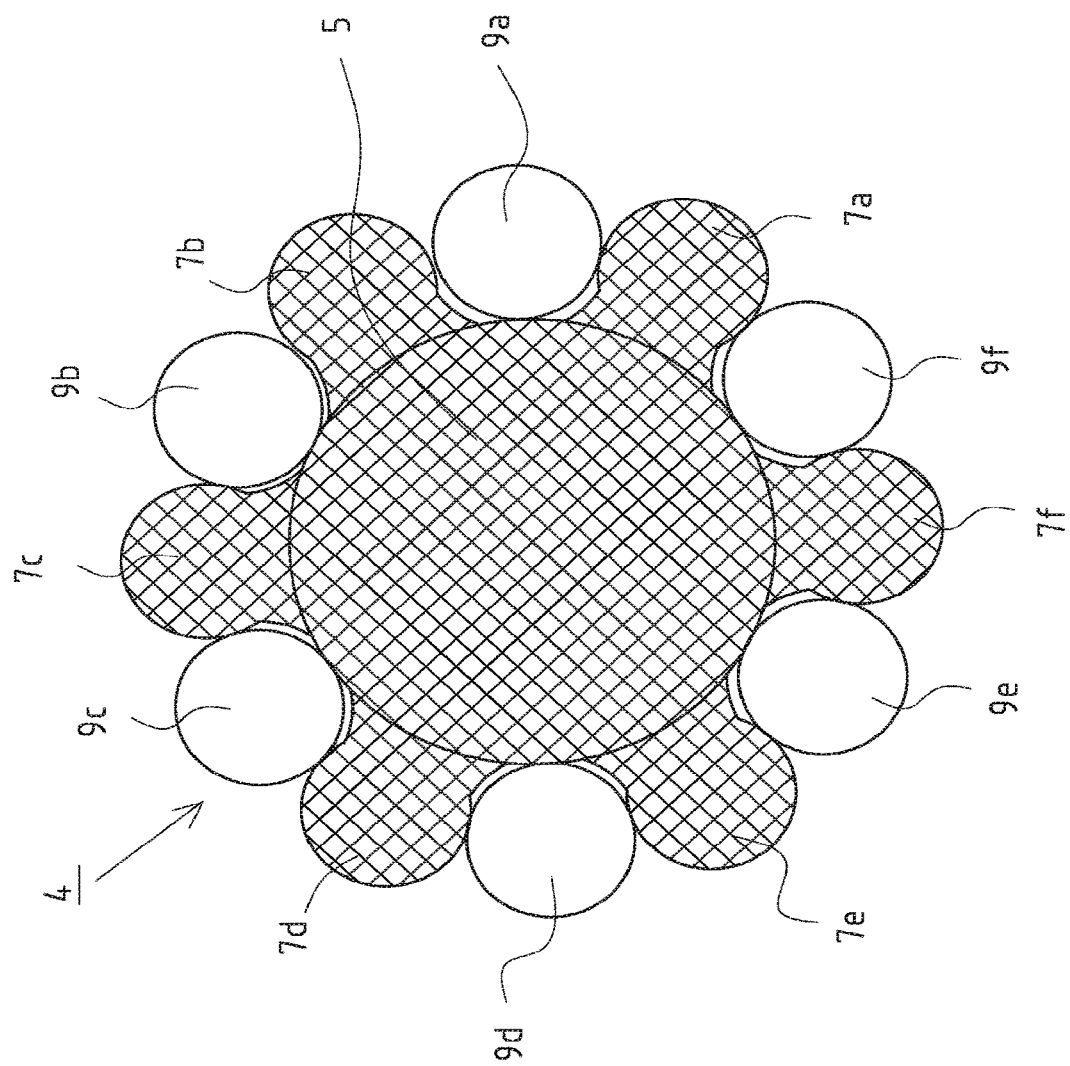
FIG. 4 shows a cross-sectional view along line B-B in FIG. 1.

FIG. 1 shows a side view of a connection structure 1 according to the disclosed embodiments, FIG. 2 shows a cross-sectional side view of the connection structure 1, FIG. 3 shows a cross-sectional view along line A-A in FIG. 1, and FIG. 4 shows a cross-sectional view along line B-B in FIG. 1.

Note that in order to clearly indicate that a first rod 3 and first metal element wires 9 as described below comprise the same material, and a second rod 5 and second metal element wires 7 as described below comprise the same material, only portions corresponding to the second rod 5 and the second metal wires 7 are shaded in FIGS. 1 to 4.

As shown in FIGS. 1 and 2, the connection structure 1 connects the first rod 3 comprising a stainless steel alloy and the second rod 5 comprising a nickel-titanium alloy. The connection structure 1 is formed of a multi-thread coil 4 formed by winding the first metal element wires 9 comprising the stainless steel alloy and the second metal element wires 7 comprising the nickel-titanium alloy, and is arranged between the first rod 3 and the second rod 5.

The multi-thread coil 4 in FIGS. 1 to 4 is formed by winding 6 first metal element wires 9 (9a, 9b, 9c, 9d, 9e, 9f) and 6 second metal element wires 7 (7a, 7b, 7c, 7d, 7e, 7f).

The first metal element wires 9 and the second metal element wires 7 are adjacently wound one by one.

As shown in FIG. 3, the first rod 3 comprising the stainless steel alloy is welded to the first metal element wires 9 (9a, 9b, 9c, 9d, 9e, 9f) comprising the stainless steel alloy, but is not welded to the second metal element wires 7 (7a, 7b, 7c, 7d, 7e, 7f) comprising the nickel-titanium alloy.

Further, with reference to FIG. 3, the first metal element wires 9 (9a, 9b, 9c, 9d, 9e, 9f) are welded to the first rod 3 so as to sandwich the second metal element wires 7 (7a, 7b, 7c, 7d, 7e, 7f) from both sides of each second metal element wire 7 at a connected portion between the first rod 3 and the multi-thread coil 4. That is, each second metal element wire 7 is contacted on both sides by first metal element wires 9.

On the other hand, the second rod 5 comprising the nickel-titanium alloy is welded to the second metal element wires 7 (7a, 7b, 7c, 7d, 7e, 7f) comprising the nickel titanium alloy, but is not welded to the first metal element wires 9 (9a, 9b, 9c, 9d, 9e, 9f) comprising the stainless steel alloy, as shown in FIG. 4.

Moreover, with reference to FIG. 4, the second metal element wires 7 (7a, 7b, 7c, 7d, 7e, 7f) are welded to the second rod 5 so as to sandwich the first metal element wires 9 (9a, 9b, 9c, 9d, 9e, 9f) from both sides of each first metal element wire 9 at a connected portion between the second rod 5 and the multi-thread coil 4.

Note that the multi-thread coil 4 in FIGS. 1 to 4 is formed by winding a total of 12 metal element wires (6 first metal element wires 9 and 6 second metal element wires 7), but the multi-thread coil 4 is not limited to this configuration. The multi-thread coil 4 can contain any number of the first metal element wires 9 and the second metal element wires 7 as long as the total number of each of the first metal element wires 9 and the second metal element wires 7 is 2 or more. However, the first metal element wires 9 and the second metal element wires 7 preferably cover the entire cross-sectional circumferences of the first rod 3 and the second rod 5 where connected.

Further, in the connection structure 1 described above, the first rod 3 comprises a stainless steel alloy, and the second rod 5 comprises a nickel-titanium alloy, and the multi-thread coil 4 is formed by winding the first metal element wires 9 comprising the stainless steel alloy and the second metal element wires 7 comprising the nickel-titanium alloy. However, the configuration is not limited to this.

For example, the first rod 3 may comprise a cobalt-chromium alloy, and the second rod 5 may comprise a nickel-titanium alloy, and the multi-thread coil 4 may be formed by winding the first metal element wires 9 comprising the cobalt-chromium alloy and the second metal element wires 7 comprising the nickel-titanium alloy. Alternatively, the first rod 3 may comprise a stainless steel alloy, and the second rod 5 may comprise a cobalt-chromium alloy, and the multi-thread coil 4 may be formed by winding the first metal element wires 9 comprising the stainless steel alloy and the second metal element wires 7 comprising the cobalt-chromium alloy.

In the connection structure 1 shown in FIGS. 1 to 4, the multi-thread coil 4 formed by winding the first element wires 9 comprising the first metal and the second element wires 7 comprising the second metal is arranged between the first rod 3 comprising the first metal such as a stainless steel alloy and the second rod 5 comprising the second metal such as a nickel-titanium alloy. Additionally, the first rod 3 is not connected to the second metal element wires 7 of the multi-thread coil 4, but is connected to the first metal element wires 9 of the multi-thread coil 4, and the second rod 5 is not connected to the first metal element wires 9 of the multi-thread coil 4, but is connected to the second metal element wires 7 of the multi-thread coil 4. This can improve the flexibility of the connected portion formed by the multi-thread coil.

Further, in the connection structure 1 according to FIGS. 1 to 4, the multi-thread coil 4 comprises the first metal element wires 9 and the second metal element wires 7 adjacently wound one by one, and the first metal element wires 9 are connected to the first rod 3 so as to sandwich the second metal element wires 7, and the second metal element wires 7 are connected to the second rod 5 so as to sandwich the first metal element wires 9. This can prevent distortion of the shape of the multi-thread coil 4 as much as possible, and can improve the flexibility of the connected portion 1.

Moreover, the connection structure 1 can improve the flexibility of the connected portion, and can also provide an appropriate connection even when dissimilar metals are used such as a stainless steel alloy and a nickel titanium alloy, which are difficult to directly connect to each other.

Figure 5:
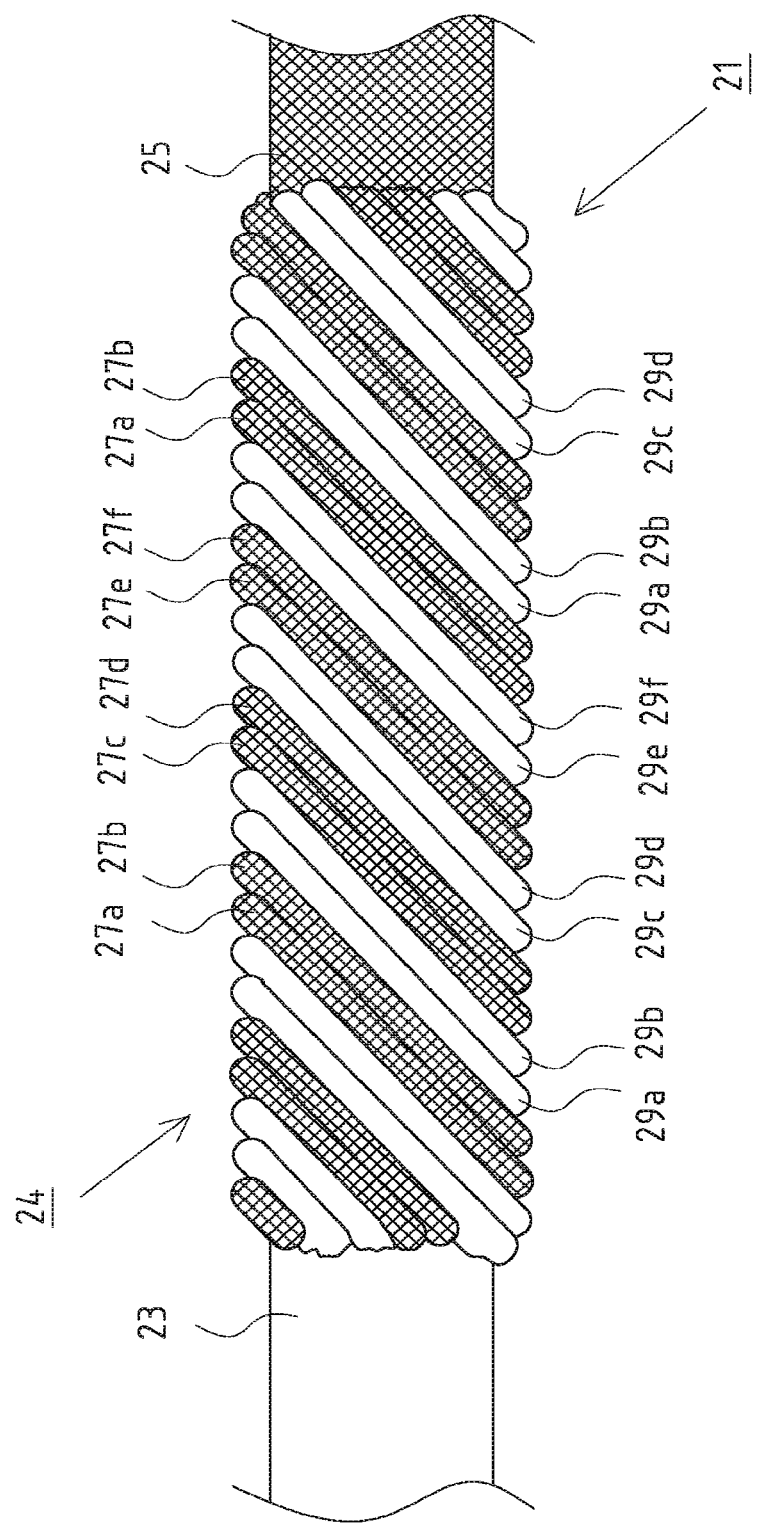
FIG. 5 shows a side view of a connection structure according to the disclosed embodiments.
Figure 6:
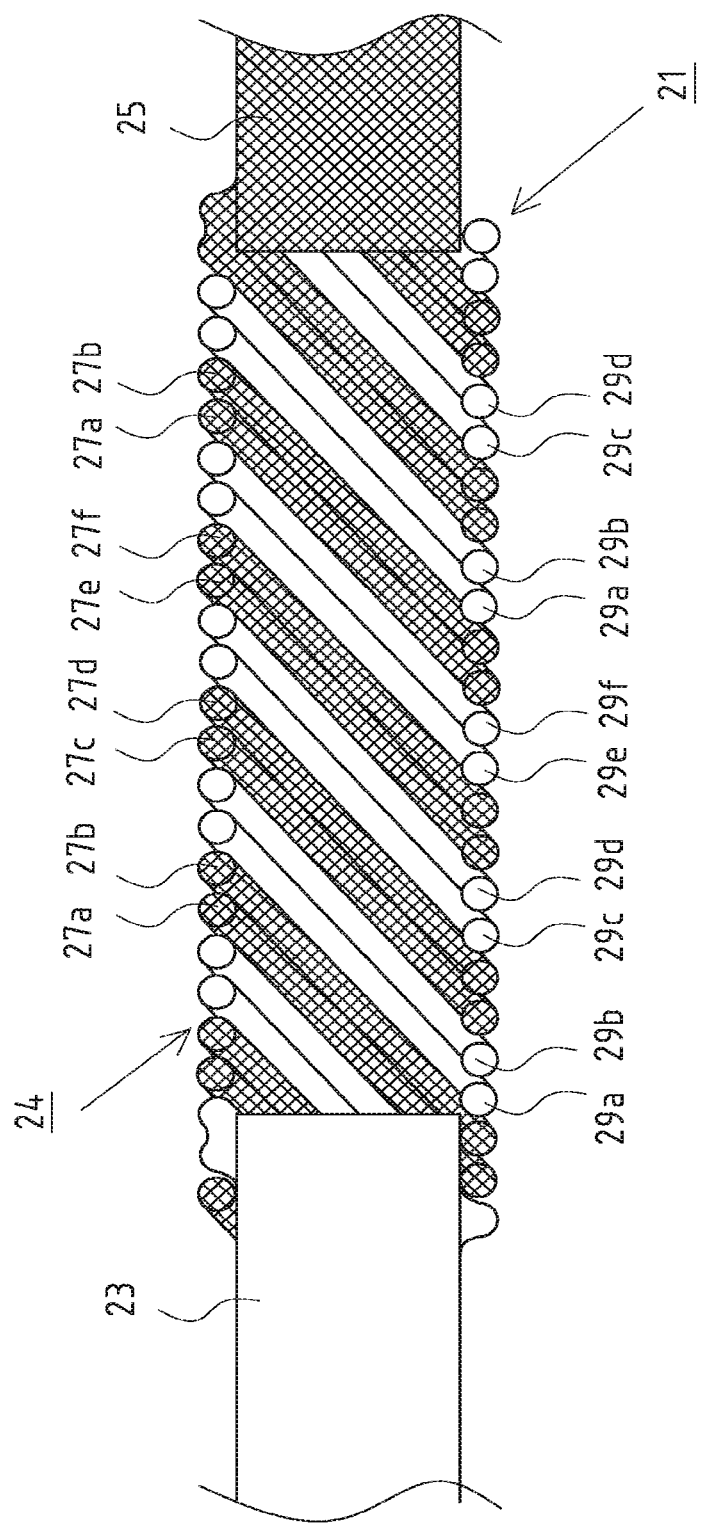
FIG. 6 shows a cross-sectional side view of the connection structure shown in FIG. 5.

FIG. 5 shows a side view of a connection structure 21 according to the disclosed embodiments, and FIG. 6 shows a cross-sectional side view of the connection structure 21.

Note that in order to clearly indicate that a third rod 23 and third metal element wires 29 as described below comprise the same material, and a fourth rod 25 and fourth metal element wires 27 as described below comprise the same material, only portions corresponding to the fourth rod 25 and the fourth metal wires 27 are shaded in FIGS. 5 and 6.

As shown in FIGS. 5 and 6, the connection structure 21 connects the third rod 23 comprising a stainless steel alloy to the fourth rod 25 comprising a nickel-titanium alloy. The connection structure 21 is formed of a multi-thread coil 24 formed by winding the third metal element wires 29 comprising the stainless alloy and the fourth metal element wires 27 comprising the nickel-titanium alloy, and is arranged between the third rod 23 and the fourth rod 25.

The multi-thread coil 24 in FIGS. 5 and 6 is formed by winding 6 third metal element wires 29 (29a, 29b, 29c, 29d, 29e, 29f) and 6 fourth metal element wires 27 (27a, 27b, 27c, 27d, 27e, 27f). Unlike the multi-thread coil 4, the multi-thread coil 24 comprises the third metal element wires 29 and the fourth metal element wires 27 adjacently wound two at a time.

The third rod 23 comprising the stainless steel alloy is welded to the third metal element wires 29 (29a, 29b, 29c, 29d, 29e, 29f) comprising the stainless steel alloy, but is not welded to the fourth metal element wires 27 (27a, 27b, 27c, 27d, 27e, 27f) comprising the nickel titanium alloy, as in the multi-thread coil 4.

Further, the third metal element wires 29 (29a, 29b, 29c, 29d, 29e, 29f) are welded to the third rod 23 so as to sandwich two of the fourth metal element wires 27 (27a, 27b, 27c, 27d, 27e, 27f) from both sides of the pair of fourth metal element wires 27 at a connected portion between the third rod 23 and the multi-thread coil 24.

On the other hand, the fourth rod 25 comprising the nickel-titanium alloy is welded to the fourth metal element wires 27 (27a, 27b, 27c, 27d, 27e, 27f) comprising the nickel titanium alloy, but is not welded to the third metal element wires 29 (29a, 29b, 29c, 29d, 29e, 29f) comprising the stainless steel alloy, as in the multi-thread coil 4.

Further, the fourth metal element wires 27 (27a, 27b, 27c, 27d, 27e, 27f) are welded to the fourth rod 25 so as to sandwich two of the third metal element wires 29 (29a, 29b, 29c, 29d, 29e, 29f) from both sides of the pair of third metal element wires 29 at a connected portion between the fourth rod 25 and the multi-thread coil 24.

Note that in the multi-thread coil 24, two of the third metal element wires 29 (29a, 29b, 29c, 29d, 29e, 29f) are paired, and two of the fourth metal element wires 27 (27a, 27b, 27c, 27d, 27e, 27f) are paired, but the configuration is not limited to this. Three of the third metal element wires 29 (29a, 29b, 29c, 29d, 29e, 29f) may be bundled, and three of the fourth metal element wires 27 (27a, 27b, 27c, 27d, 27e, 27f) may be bundled. However, the third metal element wires 29 and the fourth metal element wires 27 preferably cover the entire cross-sectional circumferences of the third rod 23 and the fourth rod 25 where connected.

Further, in the connection structure 21 described above, the third rod 23 comprises a stainless steel alloy, and the fourth rod 25 comprises a nickel-titanium alloy, and the multi-thread coil 24 is formed by winding the third metal element wires 29 comprising the stainless steel alloy and the fourth metal element wires 27 comprising the nickel-titanium alloy. However, the configuration is not limited to this.

For example, the third rod 23 may comprise a cobalt-chromium alloy, and the fourth rod 25 may comprise a nickel-titanium alloy, and the multi-thread coil 24 may be formed by winding the third metal element wires 29 comprising the cobalt-chromium alloy and the fourth metal element wires 27 comprising the nickel-titanium alloy. Alternatively, the third rod 23 may comprise a stainless steel alloy, and the fourth rod 25 may comprise a cobalt-chromium alloy, and the multi-thread coil 24 may be formed by winding the third metal element wires 29 comprising the stainless steel alloy and the fourth metal element wires 27 comprising the cobalt-chromium alloy.

In the connection structure 21 shown in FIGS. 5 and 6, the multi-thread coil 24 formed by winding the third metal element wires 29 comprising the first metal and the fourth metal element wires 27 comprising the second metal is arranged between the third rod 23 comprising the first metal such as a stainless steel alloy and the fourth rod 25 comprising the second metal such as a nickel-titanium alloy. Additionally, the third rod 23 is connected to only the third metal element wires 29 of the multi-thread coil 24, and the fourth rod 25 is connected to only the fourth metal element wires 27 of the multi-thread coil 24. This can improve the flexibility of a connected portion formed by the multi-thread coil 24.

Moreover, the connection structure 21 can improve the flexibility of the connected portion, and can also provide an appropriate connection even when dissimilar metals are used such as a stainless steel alloy and a nickel-titanium alloy, which are difficult to directly connect to each other.

Figure 7:
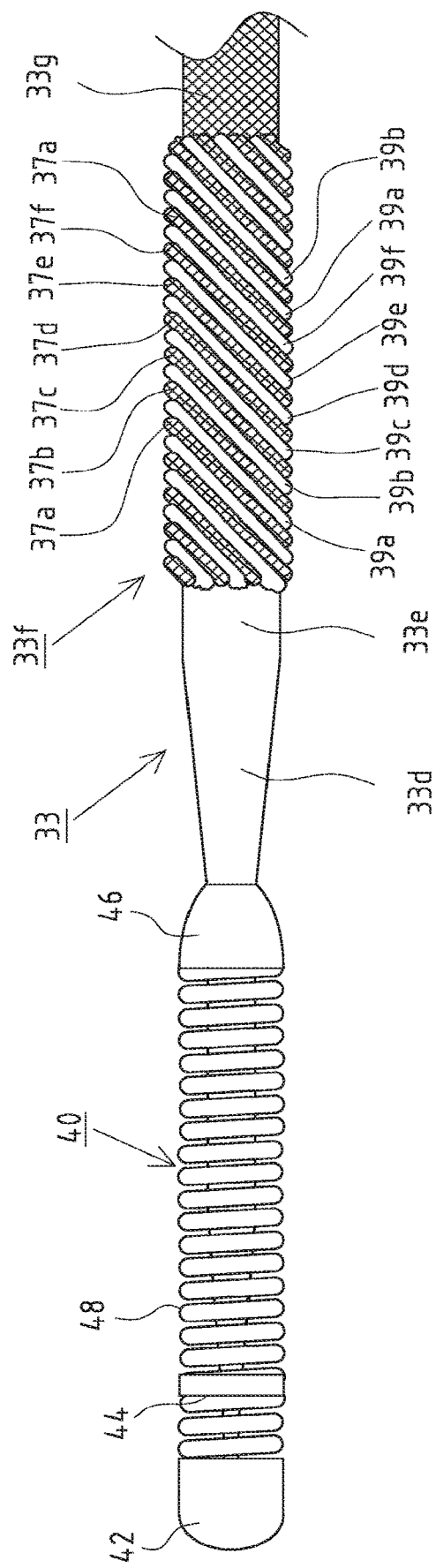
FIG. 7 shows a schematic side view of a guide wire according to the disclosed embodiments.
Figure 8:
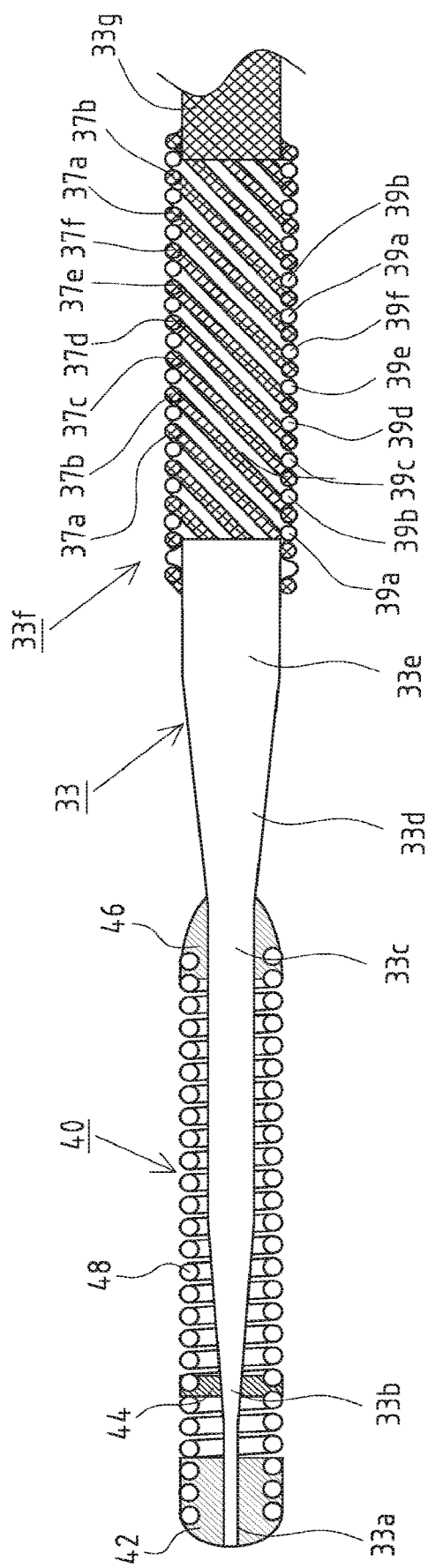
FIG. 8 shows a schematic cross-sectional side view of the guide wire shown in FIG. 7.

FIG. 7 shows a schematic side view of a guide wire 40 according to the disclosed embodiments, and FIG. 8 shows a schematic cross-sectional side view of the guide wire 40.

Note that in order to clearly indicate that a first cylinder portion 33a, a first tapered portion 33b, a second cylinder portion 33c, a second tapered portion 33d, a third cylinder portion 33e, and fifth metal element wires 39 of a core shaft 33 as described below all comprise the same material, and that a fourth cylinder portion 33g and sixth metal element wires 37 of the core shaft 33 as described below all comprise the same material, only portions corresponding the fourth cylinder portion 33g and the sixth metal element wires 37 of the core shaft 33 are shaded in FIGS. 7 and 8.

As shown in FIGS. 7 and 8, a guide wire 40 comprises the core shaft 33 and a coil body 48 covering a distal (front) end of the core shaft 33.

The coil body 48 is a single-thread coil body comprising a stainless steel alloy.

The core shaft 33 comprises, as listed from its distal end, the first cylinder portion 33a, the first tapered portion 33b, the second cylinder portion 33c, the second tapered portion 33d, the third cylinder portion 33e, the fourth cylinder portion 33g, a multi-thread coil body 33f, and the fourth cylinder portion 33g.

Here, the first cylinder portion 33a, the first tapered portion 33b, the second cylinder portion 33c, the second tapered portion 33d, and the third cylinder portion 33e form an elongated metal rod body with a round cross-section comprising a stainless steel alloy, and the fourth cylinder portion 33g is an elongated metal rod body with a round cross-section comprising a nickel-titanium alloy.

Further, the multi-thread coil 33f is formed by winding 6 fifth metal element wires 39 (39a, 39b, 39c, 39d, 39e, 39f) and 6 sixth metal element wires 37 (37a, 37b, 37c, 37d, 37e, 37f).

The coil body 48 is a single-thread coil body comprising the stainless steel alloy. A distal end of the coil body 48 is brazed to a distal end of the first cylinder portion 33a of the core shaft 33 to form a front brazing portion 42.

Further, a proximal end part of the coil body 48 is brazed to the second cylinder portion 33c of the core shaft 33 to form a proximal end brazing portion 46, and an intermediate part (a middle part) of the coil body 48 is brazed to the first tapered portion 33b of the core shaft 33 to form a middle brazing portion 44.

Further, in the multi-thread coil 33f, the fifth metal element wires 39 and the sixth metal element wires 37 are adjacently wound one by one.

The third cylinder portion 33e comprising the stainless steel alloy is welded to the fifth metal element wires 39 (39a, 39b, 39c, 39d, 39e, and 39f) comprising the stainless steel alloy of the multi-thread coil 33f, but is not welded to the sixth metal element wires 37 (37a, 37b, 37c, 37d, 37e, 37f) comprising the nickel-titanium alloy of the multi-thread coil 33f.

Further, the fifth metal element wires 39 (39a, 39b, 39c, 39d, 39e, 39f) are welded to the third cylinder portion 33e so as to sandwich the sixth metal element wires 37 (37a, 37b, 37c, 37d, 37e, 37f) from both sides of each sixth metal element wire 37 at a connected portion of the third cylinder portion 33e and the multi-thread coil 33f.

On the other hand, the fourth cylinder portion 33g comprising the nickel-titanium alloy is welded to the sixth metal element wires 37 (37a, 37b, 37c, 37d, 37e, 37f) comprising the nickel-titanium alloy of the multi-thread coil 33f, but is not welded to the fifth metal element wires 39 (39a, 39b, 39c, 39d, 39e, 39f) comprising the stainless steel alloy of the multi-thread coil 33f.

Further, the sixth metal element wires 37 (37a, 37b, 37c, 37d, 37e, 37f) are welded to the fourth cylinder portion 33g so as to sandwich the fifth metal element wires 39 (39a, 39b, 39c, 39d, 39e, 39f) from both sides of each fifth metal element wire 39 at a connected portion of the fourth cylinder portion 33g and the multi-thread coil 33f.

Note that the multi-thread coil 33f shown in FIGS. 7 and 8 is formed by winding a total of 12 metal element wires (6 fifth metal element wires 39 and 6 sixth metal element wires 37, but the multi-thread coil 33f is not limited to this configuration. The multi-thread coil 33f can contain any number of the fifth metal element wires 39 and the sixth metal element wires 37 as long as the total number of each of the fifth metal element wires 39 and the sixth metal element wires 37 is 2 or more. However, the fifth metal element wires 39 and the sixth metal element wires 37 preferably cover the entire cross-sectional circumferences of the third cylinder portion 33e and the fourth cylinder portion 33g of the core shaft 33 where connected.

Further, in the guide wire 40 shown in FIGS. 7 and 8, the third cylinder portion 33e of the core shaft 33 comprises a stainless steel alloy, and the fourth cylinder portion 33g of the core shaft 33 comprises a nickel-titanium alloy, and the multi-thread coil 33f is formed by winding the fifth metal element wires 39 comprising the stainless steel alloy and the sixth metal element wires 37 comprising the nickel-titanium alloy. However, the configuration is not limited to this.

For example, the third cylinder portion 33e of the core shaft 33 may comprise a cobalt-chromium alloy, and the fourth cylinder portion 33g of the core shaft 33 may comprise a nickel-titanium alloy, and the multi-thread coil 33f may be formed by winding the fifth metal element wires 39 comprising the cobalt-chromium alloy and the sixth metal element wires 37 comprising the nickel-titanium alloy. Alternatively, the third cylinder portion 33e of the core shaft 33 may comprise a stainless steel alloy, and the fourth cylinder portion 33g of the core shaft 33 may comprise a cobalt-chromium alloy, and the multi-thread coil 33f may be formed by winding the fifth metal element wires 39 comprising the stainless steel alloy and the sixth metal element wires 37 comprising the cobalt-chromium alloy.

In the guide wire 40 shown in FIGS. 7 and 8, the multi-thread coil 33f formed by winding the fifth metal element wires 39 comprising the first metal and the sixth metal element wires 37 comprising the second metal is arranged between the third cylinder portion 33e of the core shaft 33 comprising the first metal such as a stainless steel alloy and the fourth cylinder portion 33g comprising the second metal such as a nickel titanium alloy. Additionally, the third cylinder portion 33e of the core shaft 33 is connected to only the fifth metal element wires 39 of the multi-thread coil 33f, and the fourth cylinder portion 33g is connected to only the sixth metal element wires 37 of the multi-thread coil 33f This can improve the flexibility of the connected portion formed by the multi-thread coil 33f, enabling the guide wire 40 to easily follow along a winding blood vessel.

Further, in the guide wire 40 shown in FIGS. 7 and 8, the multi-thread coil 33f comprises the fifth metal element wires 39 and the sixth metal element wires 37 adjacently wound one by one, and the fifth metal element wires 39 are connected to the third cylinder portion 33e of the core shaft 33 so as to sandwich the sixth metal element wires 37, and the sixth metal element wires 37 are connected to the fourth cylinder portion 33g so as to sandwich the fifth metal element wires 39. This can prevent distortion of the shape of the multi-thread coil 33f as much as possible, and can also improve the flexibility of the connected portion.

Note that as described above, an example is presented where a connection structure corresponding to the connection structure 1 is used in the guide wire 40, but the configuration is not limited to this. The connection structure 24 may also be used in a guide wire. In that case, the advantageous effects of the connection structure 24 will be manifested therein.

Guide wires according to the disclosed embodiments are described above, but the present invention shall not be limited to the above examples. Various modifications can be made to the above-described examples without departing from the spirit of the present invention.

For example, the metal element wires 7, 9, 27, 29, 37, 39 of the multi-thread coil 4, 24, 33f are welded to the rod bodies 3, 5, 23, 25 or the elongated metal rod bodies forming the core shaft 33 in the embodiments described above, but they may be connected by a method other than welding. However, welding is preferred considering that metals can be easily connected.

What is claimed is:

1. A connection structure comprising:
   a first metal body comprising a first metal;
   a second metal body comprising a second metal; and
   a multi-thread coil wrapped around a portion of an outermost circumferential surface of a cylindrical distal end of the first metal body and an outermost circumferential surface of a cylindrical proximal end of the second metal body, the multi-thread coil comprising:
   a first element wire comprising the first metal; and
   a second element wire comprising the second metal,
   wherein:
   the first element wire is connected to the outermost circumferential surface of the distal end of first metal body, and
   the second element wire is connected to the outermost circumferential surface of the proximal end of the second metal body.

2. The connection structure according to claim 1, wherein:
   the first metal body is not connected to the second element wire, and
   the second metal body is not connected to the first element wire.

3. The connection structure according to claim 1, wherein:
   the first element wire and the second element wire are alternately disposed, and
   the first element wire is connected to the outermost circumferential surface of the distal end of the first metal body so as to sandwich the second element wire, and the second element wire is connected to the outermost circumferential surface of the proximal end of the second metal body so as to sandwich the first element wire.

4. The connection structure according to claim 2, wherein:
   the first element wire and the second element wire are alternately disposed, and
   the first element wire is connected to the outermost circumferential surface of the distal end of the first metal body so as to sandwich the second element wire, and the second element wire is connected to the outermost circumferential surface of the proximal end of the second metal body so as to sandwich the first element wire.

5. The connection structure according to claim 1, wherein the first metal is a stainless steel alloy, and the second metal is a nickel-titanium alloy.

6. The connection structure according to claim 2, wherein the first metal is a stainless steel alloy, and the second metal is a nickel-titanium alloy.

7. The connection structure according to claim 3, wherein the first metal is a stainless steel alloy, and the second metal is a nickel-titanium alloy.

8. The connection structure according to claim 4, wherein the first metal is a stainless steel alloy, and the second metal is a nickel-titanium alloy.

9. A guide wire comprising:
   a core shaft comprising the connection structure according to claim 1; and
   a coil body covering a distal portion of the core shaft.

10. A guide wire comprising:
    a core shaft comprising the connection structure according to claim 2; and
    a coil body covering a distal portion of the core shaft.

11. A guide wire comprising:
    a core shaft comprising the connection structure according to claim 3; and
    a coil body covering a distal portion of the core shaft.

12. A guide wire comprising:
a core shaft comprising the connection structure according to claim 4; and
a coil body covering a distal portion of the core shaft.

13. A guide wire comprising:
a core shaft comprising the connection structure according to claim 5; and
a coil body covering a distal portion of the core shaft.

14. The connection structure according to claim 1, wherein:
the first element wire is connected to the outermost circumferential surface of the distal end of the first metal body by welding, and
the second element wire is connected to the outermost circumferential surface of the proximal end of the second metal body by welding.

* * * * *